(12) United States Patent
Doris et al.

(10) Patent No.: US 12,390,130 B2
(45) Date of Patent: Aug. 19, 2025

(54) WEARABLE DEVICE FOR MONITORING BODILY FLUIDS

(71) Applicant: INTERNATIONAL BUSINESS MACHINES CORPORATION, Armonk, NY (US)

(72) Inventors: Bruce B. Doris, Hartsdale, NY (US); Sufi Zafar, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 894 days.

(21) Appl. No.: 17/572,038

(22) Filed: Jan. 10, 2022

(65) Prior Publication Data

US 2022/0125347 A1  Apr. 28, 2022

Related U.S. Application Data

(63) Continuation of application No. 15/175,220, filed on Jun. 7, 2016, now Pat. No. 11,241,174.

(51) Int. Cl.
*A61B 5/145* (2006.01)
*A61B 5/00* (2006.01)
*A61B 5/1477* (2006.01)

(52) U.S. Cl.
CPC ...... *A61B 5/14521* (2013.01); *A61B 5/14517* (2013.01); *A61B 5/14546* (2013.01); *A61B 5/1477* (2013.01); *A61B 5/6832* (2013.01); *A61B 5/0022* (2013.01)

(58) Field of Classification Search
CPC ............ A61B 5/14521; A61B 5/14546; A61B 5/1477; A61B 5/6832
See application file for complete search history.

(56) References Cited

U.S. PATENT DOCUMENTS

| | | | |
|---|---|---|---|
| 4,457,748 A | 7/1984 | Lattin et al. | |
| 4,846,182 A | 7/1989 | Fogt et al. | |
| 5,976,499 A | 11/1999 | Rubenstein et al. | |
| 6,042,543 A | 3/2000 | Warwick et al. | |
| 6,139,538 A * | 10/2000 | Houghton | A61N 1/306 |
| | | | 604/21 |
| 8,215,192 B2 | 7/2012 | Erez et al. | |
| 2010/0130843 A1 | 5/2010 | Caceres Galvez et al. | |

(Continued)

FOREIGN PATENT DOCUMENTS

WO  2014194537  12/2014

OTHER PUBLICATIONS

Constantinescu et al. "The Sweat Test for Quantification of Electrolytes". Laboratory Medicine. vol. 27, No. 7, Jul. 1996. (Year: 1996).*

(Continued)

*Primary Examiner* — Christian Jang
(74) *Attorney, Agent, or Firm* — Tutunjian & Bitetto, P.C.; Samuel Waldbaum

(57) ABSTRACT

A wearable monitoring system includes a first flexible substrate encapsulating a current ramping system to provide a current to an electrode in direct contact with a predetermined location of skin of a user to promote bodily fluid secretion, and a second flexible substrate placed over the predetermined location, the second flexible substrate having an integrated electrochemical sensor to determine bodily fluid concentration levels secreted through the skin.

20 Claims, 4 Drawing Sheets

(56) References Cited

U.S. PATENT DOCUMENTS

2013/0150691 A1* 6/2013 Pace ............... A61B 5/150305
                                                          600/347
2014/0012114 A1* 1/2014 Zevenbergen ..... A61B 5/14517
                                                          600/346
2015/0112164 A1  4/2015 Heikenfeld et al.
2018/0235522 A1* 8/2018 Heikenfeld ........ A61B 5/14521

OTHER PUBLICATIONS

List of IBM Patents or Patent Applications Treated as Related dated Jan. 10, 2022, 2 pages.

Legrys, et al., "Diagnostic Sweat Testing: The Cystic Fibrosis Foundation Guidelines", The Journal of Pediatrics, Jul. 2007, pp. 85-89.

Mattar, et al., "Comparison Between Classic Gibson And Cooke Technique And Sweat Conductivity Test In Patients With And Without Cystic Fibrosis", Journal de Pediatria, Nov. 2010, pp. 109-114, vol. 86, No. 2.

Mishra, et al., "The Relevance of Sweat Testing for the Diagnosis of Cystic Fibrosis in the Genomic Era", Clin Biochem Rev, Nov. 2005, pp. 135-153, vol. 26.

Zafar, et al., "A Comparison Between Bipolar Transistor and Nanowire Field Effect Transistor Biosensors", Applied Physics Letters 106, Feb. 2015, 5 pages.

* cited by examiner

WEARABLE DEVICE FOR MONITORING BODILY FLUIDS

BACKGROUND

Technical Field

The present invention relates to bodily fluid monitoring systems, and more particularly to systems and methods for monitoring bodily fluids using a low-profile, low cost wearable device.

Description of the Related Art

Monitoring of various vital signs of an individual, such as heart rate sensing and blood pressure monitoring, provides useful medical information to an individual and/or medical professional to determine whether the individual is suffering from any health conditions, such as an illness, injury, impairment, and/or physical or mental conditions. Abnormal concentration levels of certain substances secreted by various glands on the human body may be a predictor of certain illnesses. For example, abnormal chloride concentration levels, abnormally high levels of electrolytes, and/or abnormal sweat gland function may be an indicator of Cystic Fibrosis. Monitoring and/or sensing bodily fluids for individuals may provide early detection of emerging health conditions.

SUMMARY

A wearable monitoring system includes a first flexible substrate encapsulating a current ramping system to provide a current to at least one electrode in direct contact with a predetermined location of skin of a user to promote bodily fluid secretion, and a second flexible substrate placed over the predetermined location, the second flexible substrate having an integrated electrochemical sensor to determine bodily fluid concentration levels secreted through the skin.

Another wearable monitoring system includes a first flexible substrate encapsulating a current ramping system to provide a current to at least one electrode in direct contact with a predetermined location of skin of a user to promote bodily fluid secretion, wherein the first flexible substrate includes at least one chemical substance such that the at least one chemical substance is applied directly on the predetermined location of the skin, and a second flexible substrate placed over the predetermined location, the second flexible substrate having an integrated electrochemical sensor to determine bodily fluid concentration levels secreted through the skin, wherein the integrated electrochemical sensor is disposed on a sensing surface, the sensing surface having a silver chloride (AgCl) material for chloride ion detection.

A method for monitoring bodily fluids includes adhering a monitoring system to skin of a user using a first flexible substrate to encapsulate a current ramping system, powering the current ramping system using a portable power source disposed in or on the first flexible substrate to provide a current to at least one electrode in direct contact with a predetermined location of the skin of the user to promote bodily fluid secretion, and monitoring bodily fluid concentration levels secreted through the skin using a second flexible substrate of the monitoring system placed over the predetermined location, the second flexible substrate having an integrated electrochemical sensor to determine the bodily fluid concentration levels secreted through the skin.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

Figure 1:
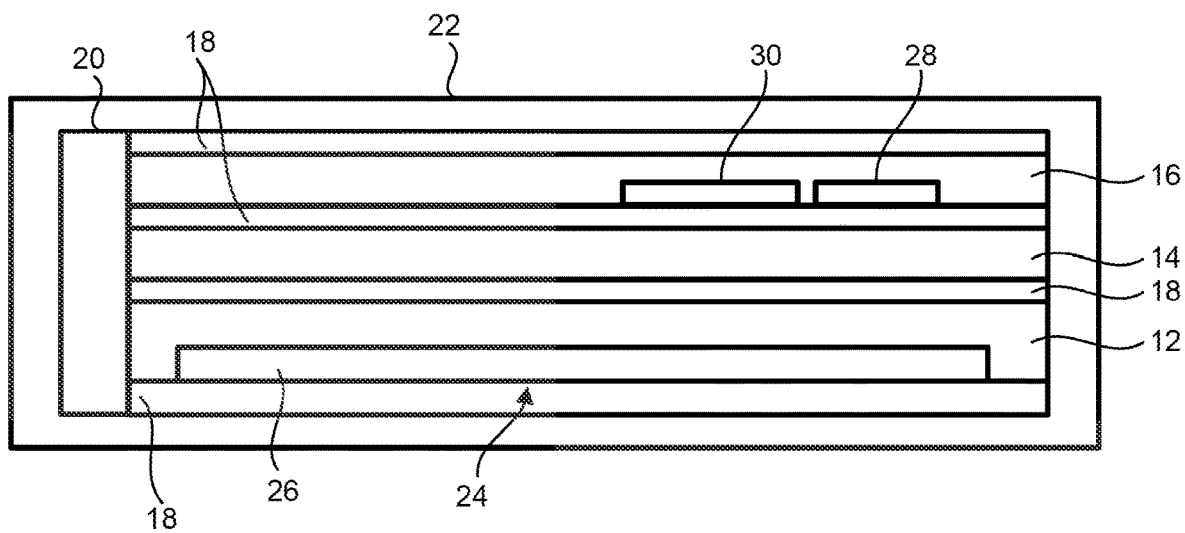
FIG. 1 is a cross-sectional view of a monitoring system for monitoring bodily fluids installed on a user's skin in accordance with the present principles.

In accordance with the present principles, systems and methods are provided for a wearable bodily fluid monitoring device. The wearable device may be attached to the skin of a user and continuously monitor bodily fluids of a user. The wearable device is low-profile and compatible with everyday activities. The wearable device may include a transmitter to transmit data to a remote receiver. The receiver may include a smart phone, computer or a processing center. The wearable device may include one or more integrated circuit chips. The integrated circuit chip, which may include electrode ramping circuitry, may be included in a system that attaches to the skin of the user to apply a current such that a substance permeates into the user's skin to promote secretions from the user's skin. The system may further include an electrochemical sensor, such as a bipolar junction transistor, to detect and/or measure concentration levels in bodily fluids secreted by the user's skin. The system may include memory to store the data and may include signal processing capabilities. In other embodiments, an antenna is included in the system to transmit the data remotely. The signal processing and storage may be processed remotely as well.

The wearable monitoring system may include one or more integrated circuit chips and/or electrochemical sensors placed on the user. The wearable monitoring system includes a portable, wearable, disposable, rechargeable and/or alternate power source connected to the integrated circuit chip. A flexible substrate is configured to encapsulate and affix the integrated circuit chip and/or electrochemical sensor to the skin of the user.

In one useful embodiment, a wearable system for monitoring of bodily fluids includes a bipolar junction transistor having a reference electrode and a sensing surface embedded in a hydrogel filled capsule, the hydrogel fill capsule being removed prior to placing the reference electrode and sensing surface in direct contact with the user's skin. A complementary semiconductor chip for power management and memory storage is coupled to the bipolar junction transistor. A flexible substrate provides adhesion to the skin of a user and supports the system to make it wearable. An antenna and a thin film battery may be built into the flexible substrate.

The system is employed to monitor and detect bodily fluids secreted from a user's skin. A footprint and cost of such monitoring system is small enough that the system can be disposable and can be driven by portable electronics. Once data (e.g., concentration levels) of the bodily fluids is detected and/or measured, the data can then be presented visually to medical professionals, health care professionals, the user or designated individuals. Such data can enable computer-assisted diagnostics or first screening of possibly serious problems, such data can be encrypted to ensure privacy and security of the data and user or patient and can be stored locally, used in local computation/analysis and/or sent to data storage in the home, hospital, private practice or data center or cloud data space with any appropriate authorizations for access.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a non-volatile electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a phase change memory (PCM) device, a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that the present invention will be described in terms of a given illustrative architecture; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The present embodiments may include a design for an integrated circuit chip, which may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a cross-sectional view of an exemplary embodiment for a wearable monitoring system 100 is illustratively shown for gathering bodily fluid information from a user in accordance with the present principles. System 100 includes a plurality of flexible substrates including a chemical layer 12, an intermediary layer 14, and a sensing layer 16. In some embodiments, the chemical layer 12, the intermediary layer 14, and the sensing layer 16 may be separated from each other by a protection layer 18 disposed between each of the flexible substrates. The protection layer 18 may be a flexible substrate that prevents the chemical layer 12, the intermediary layer 14, and the sensing layer 16 from coming into direct contact with each other. The protective layer 18 may include various materials, including a biocompatible impermeable membrane, such as a cotton gauze with alcohol covered by a plastic and/or polyurethane coated paper.

In some embodiments, the chemical layer 12, the intermediary layer 14, and the sensing layer 16 may be attached to a hinge layer 20. The hinge layer 20 may attach each of the flexible substrates 12, 14, 16 to form a single integrated monitoring device 100. In an embodiment, the hinge layer 20 may include a perforation at the interface of the hinge layer 20 and each of the flexible substrates 12, 14, 16 such that one or more of the flexible substrates 12, 14, 16 may be selectively detached by tearing the one or more flexible substrates at the interface. The chemical layer 12, intermediary layer 14, sensing layer 16, protection layer(s) 18, and/or hinge layer 20 may be temporarily housed in an enclosure 22 prior to use. The enclosure 22 may be waterproof, airtight and/or chemically resistant to outside contamination prior to use of the wearable monitoring system 100.

The chemical layer 12 may include a chemical substance 24 applied to the surface thereof that may be applied directly onto the skin via the wearable monitoring system 100. For example, the chemical substance 24 may be applied on the chemical layer 12 on a side opposite the intermediate layer 14. In some embodiments, the chemical layer 12 may include a chemical substance 24 to promote sweat production and/or bodily fluids to secrete from the user's skin. For example, the chemical substance 24 may include a gel having approximately 2-5 grams per liter (g/L) of pilocarpine nitrate. The chemical substance 24 may be disposed on the chemical layer 12 such that the chemical substance 24 surrounds a pair of electrodes (not shown), such as a positive and negative terminal, which will be described in further detail below. The chemical substance 24 on the chemical layer 12 may diffuse and/or be absorbed into the user's skin so as to promote bodily fluid secretion by the user.

In a further embodiment, the chemical layer 12 may further include a detachable alignment layer 26 to serve as a reference for an area on the user's skin in which the chemical layer 12 and/or chemical substance 24 was applied. For example, the alignment layer 26 may mark and/or otherwise indicate a boundary within which the chemical layer 12 and/or the chemical substance 24 (e.g., sweat promoting substance) has been applied. The alignment layer 26 may be a non-permanent image (e.g., a border resembling a rectangle, square, circle, etc.) which is detachable from the chemical layer 12 and which adheres to the user's skin temporarily.

In some embodiments, the alignment layer 26 may be a press-on decal safe for direct dermal contact. The alignment layer 26 may include a semi-permeable and/or a permeable material. In some embodiments, the alignment layer 26 may be a partial layer such that regions inside and outside of the marker 26 are in direct contact with the chemical layer 12 and/or subsequent layers of the wearable monitoring system 100. After the chemical layer 12 has been in contact with the user's skin for a period of time, the chemical layer 12 may be removed while the alignment layer 26 may detach from the chemical layer 12 and remain on the user's skin.

The intermediary layer 14 may be disposed between the chemical layer 12 and the sensing layer 16. In an embodiment, the intermediary layer 14 may include a cleansing substance which may be applied to the user's skin. For example, the intermediary layer 14 may include one or more cleaning agents, such as alcohol, di-ionized water, etc., to cleanse the user's skin. In some embodiments, the intermediary layer 14 may remove all or some of the chemical substance 24 applied by the chemical layer 12. In a further embodiment, the one or more cleaning agents on the intermediary layer 14 may prevent residual current flow of the chemical layer 12. In an alternate embodiment, the intermediary layer 14 may include an adhesive substance. For example, the intermediary layer 14 may include an adhesive agent to remove one or more layers of hair and/or skin to prepare the user's skin for application of the sensing layer 16.

The sensing layer 16 may include at least one sensor 28 that touches the skin of the user. The sensor 28 may include contacts having a corrosion resistant material or metal. In some embodiments, the sensor 28 may be bonded to the sensing layer 16. The sensor 28 may, in some embodiments, include an electrochemical sensor to detect and/or monitor amounts of and/or concentration levels of bodily fluids (e.g., sweat) secreted by the user through the user's skin. For example, the sensor 28 may detect an amount of bodily fluids secreted, such amounts including measurement in milligrams, microliters, etc. In some embodiments, the sensor 28 may detect and/or measure chloride concentration levels in the bodily fluids.

In a further embodiment, the sensor 28 may protrude from the underlying surface of the sensing layer 16 such that the sensor 28 is in direct contact with the user's skin. In a further embodiment, the sensor 28 may be encapsulated in a temporary hydrogel layer (not shown). The hydrogel layer may be filled with water, saline, or other solution to increase the shelf-life of the sensor 28. Before the sensor 28 is applied to the user's skin, the hydrogel layer may be removed.

The sensing layer 16 may further include radio frequency (RF) capability to wirelessly transmit bodily fluid information to a remote location for analysis. For example, the sensing layer 16 may be connected to a radio frequency (RF) transmitter 30. The RF transmitter device 30 may be coupled to the sensor 28 and may transmit chloride concentration data in the user's sweat to a mobile telephone or computer for analysis. The RF transmitter 30 may gather information generated from the sensor 28. The sensor 28 may include a bipolar junction transistor (BJT) sensor similar to a field-effect transistor (FET) sensor. During sensing, a reference electrode and a collector electrode of the sensor 28 are set to 0 Volts (V). In some embodiments, the emitter is biased to −0.5V when the sensor 28 includes a npn BJT. The BJT sensor 28 may be connected to CMOS circuits, including A/D converter, digital processor, battery and/or RF module 30 which may transmit the information to a mobile phone or remote computer. The BJT sensor 28 comes into contact with the user's sweat but may be isolated from the CMOS circuits by a layer of silicon nitride. Metal vias on layers about the silicon nitride may be formed to make contact to the various nodes of the BJT sensor 28 to apply and sense voltage and currents in the BJT sensor 28.

System 100 may be powered using a battery, a photovoltaic cell, a battery-free tag or other portable energy device. The battery-free tag may include an antenna on one or more layers of the flexible substrates 12, 14, 16 that may be employed to harvest energy from RF transmitters to power the system. The RF transmitters may include energy from cell phones or dedicated wireless RF transmitters that may be fixed or portable to power the system 100.

In accordance with the present principles, one or more of the flexible substrates 12, 14, and/or 16 of the system 100 is adhered to a user. Upon activation, the system 100 begins to monitor and/or detect bodily fluids and/or bodily fluid concentration levels secreted out from the user's skin, such as sweat. The bodily fluids are employed to monitor health, status and/or functionality by analyzing the measured bodily fluid concentration levels directly at the user's skin. The sensor 28 measures the bodily fluid concentration levels, which may be transmitted by the RF transmitter 30. The RF transmitter 30 may be programmed to monitor the bodily fluids to determine changes or simply to collect data.

The monitoring system 100 includes several flexible substrates and/or layers suitable for wearing on the user's skin throughout the day and/or night. The flexible substrates 12, 14, 16 may include thicknesses of 0.05 to 0.2 mm in thickness; however larger or smaller dimensions are contemplated, and in one useful embodiment, the system 100 is less than 0.8 mm in height (e.g., off the skin). In some embodiments, the monitoring system 100 includes lateral dimensions of approximately 3 to 6 inches in length and 0.5 to 4 inches in width. The flexible substrates 12, 14, and 16 may include a breathable fabric or may include a water resistant material.

The wearable system 100 is configured for continuous monitoring of bodily fluids. The system 100 may be employed for medical monitoring, baseline monitoring, activity monitoring, informational monitoring, etc. The system 100 may be installed for minutes, hours, days, weeks or longer. The system 100 may be disposable, re-useable, partially disposable and partially re-useable. The system 100 may be combined with other sensor functions, data analysis and/or communications. The system 100 may be connected as a skin wearable patch. Due to the low profile, the system 100 may be left installed during sleep or other activities.

Figure 2:
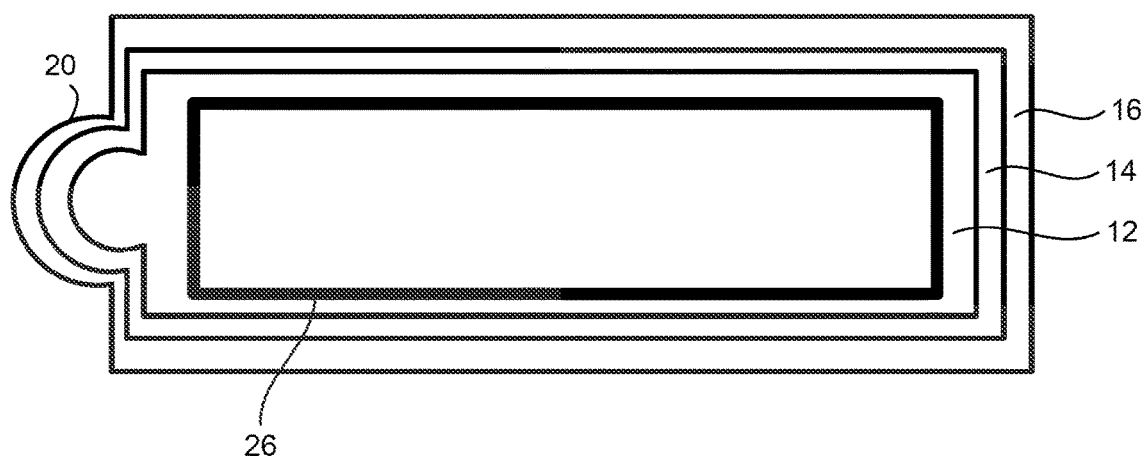
FIG. 2 is a bottom view of a monitoring system for monitoring bodily fluids installed on a user's skin in accordance with the present principles.

Referring to FIG. 2, a bottom view of the wearable monitoring system 100 is illustrated in accordance with the present principles. Each of the flexible substrates 12, 14, 16 may be connected by the hinge layer 20. In an alternate embodiment, each of the flexible substrates 12, 14, 16 may include a layer within the hinge layer 20, as shown in FIG. 2. For example, the hinge layer 20 may include multiple layers such that each of the flexible substrates 12, 14, 16 includes an integrated tab (e.g., one of the multiple layers in the hinge layer 20). The plurality of tabs may be coupled to each other such that the plurality of tabs forms the hinge layer 20. In some embodiments, the tab may include and/or provide additional functionality, as will be described in further detail below. As illustrated in FIG. 2, the flexible substrates 12, 14, 16 may include incrementally larger layers such that the chemical layer 12 is smaller than the sensing layer 16; however similar dimensions for the flexible substrates 12, 14, 16 are contemplated such that each of the flexible substrates 12, 14, 16 are the same size. In FIG. 2, the alignment layer 26 (e.g., marker) is illustrated as a rectangular decal which, when applied to the user's skin, may remain on the user's skin after removal of one or more of the flexible substrates 12, 14, 16.

In an embodiment, the hinge layer 20 may include an adhesive agent such that alignment between the flexible substrates 12, 14, 16 is maintained during application of each of the flexible substrates 12, 14, 16. The adhesive agent on the hinge layer 20 may act as a fixed point with a hinge interface such that after the chemical layer 12 and/or after the intermediary layer 14 is applied and removed, the sensing layer 16 may be aligned to the user's skin in a self-aligned manner to ensure that the sensing layer 16 detects and/or measures bodily fluids in the region where the chemical layer 12 and/or chemical substance 24 was applied.

Figure 3:
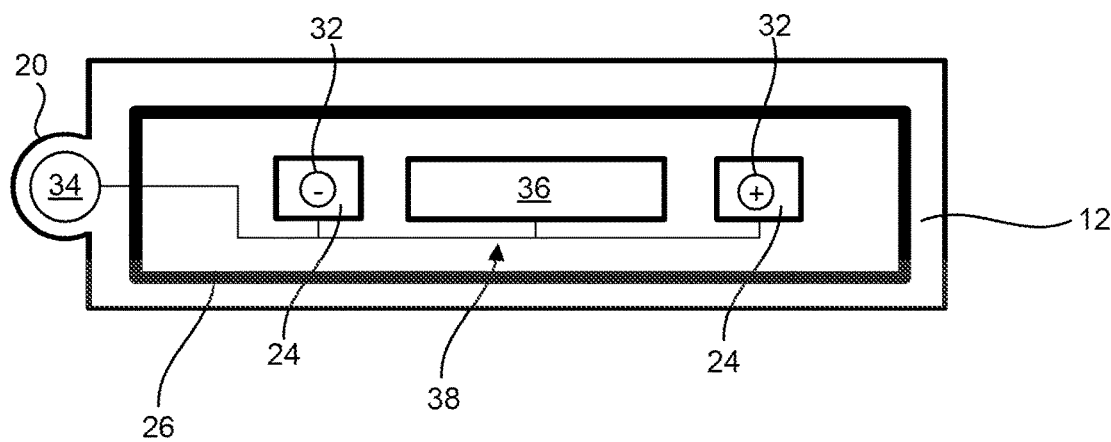
FIG. 3 is a bottom view of a monitoring system for monitoring bodily fluids installed on a user's skin in accordance with the present principles.

Referring to FIG. 3, a detailed bottom view of the chemical layer 12 of the wearable monitoring system 100 is illustrated in accordance with the present principles. As described above, the chemical layer 12 may include a chemical substance 24, such as a gel pad having approximately 2-5 g/L of pilocarpine nitrate (e.g., an electrolyte), to promote sweat production and/or bodily fluids to secrete from the user's skin. It should be noted that other chemical substances and/or concentration levels of the chemical substance are contemplated. The chemical substance 24 is applied directly to the user's skin by placing the chemical layer 12 directly on the user. In an embodiment, the chemical substance 24 may be disposed on the entire and/or partial chemical layer 12, such as within the alignment layer 26. In some embodiments, the chemical substance 24 may be disposed on areas surrounding electrodes 32, such as a positive and negative terminal. The positive and negative electrodes 32 may be copper or stainless steel, however other materials for the electrodes 32 are contemplated.

The chemical layer 12 and/or hinge layer 20 may include a battery 34 having an on/off switch. When the battery 34 is activated, a small current is applied between the electrodes 32 through connections 38. The current may include an approximate range of 0 to 5 milliamperes (mA), with 0.5 mA to 4 mA being preferable so as not to cause harm to the user. In some embodiments, the current is incrementally ramped slowly from a current of 0.5 mA to a current of 4 mA by using, for example, an electrode ramping circuitry 36 coupled to the electrodes 32 and battery 34 through connections 38. The electrode ramping circuitry 36 may include a capacitor charged by a resistance along with a discharge transistor. To improve linearity, the electrode ramping circuitry 36 may include a bootstrap ramp generator, which may include a transistor or an integrated circuit (IC) operational amplifier. The current forces the positive charged pilocarpine ions (e.g., the chemical substance 24 surrounding the positive electrode 32) to move outward from the positive electrode 32 and be absorbed into the skin of the user where intercellular calcium is increased and a calcium activated chloride channel in the user's skin is opened where sweat is produced. The electrodes 32 and/or chemical layer 12 may be removed after a period of time (e.g., five minutes) sufficient to promote bodily fluids to secrete from the user's skin.

In some embodiments, the chemical layer 12 may include a detachable alignment layer 26. The alignment layer 26 may be a decal, sticky tape, or similar functioning devices to indicate a boundary within which the sweat promoting chemical substance 24 has been applied. In an embodiment, the alignment layer may detach from the chemical layer 12 and remain on the user's skin such that subsequent layers of the system 100 may be placed in close proximity to the location on the user where the chemical layer 12 was previously placed.

Figure 4:
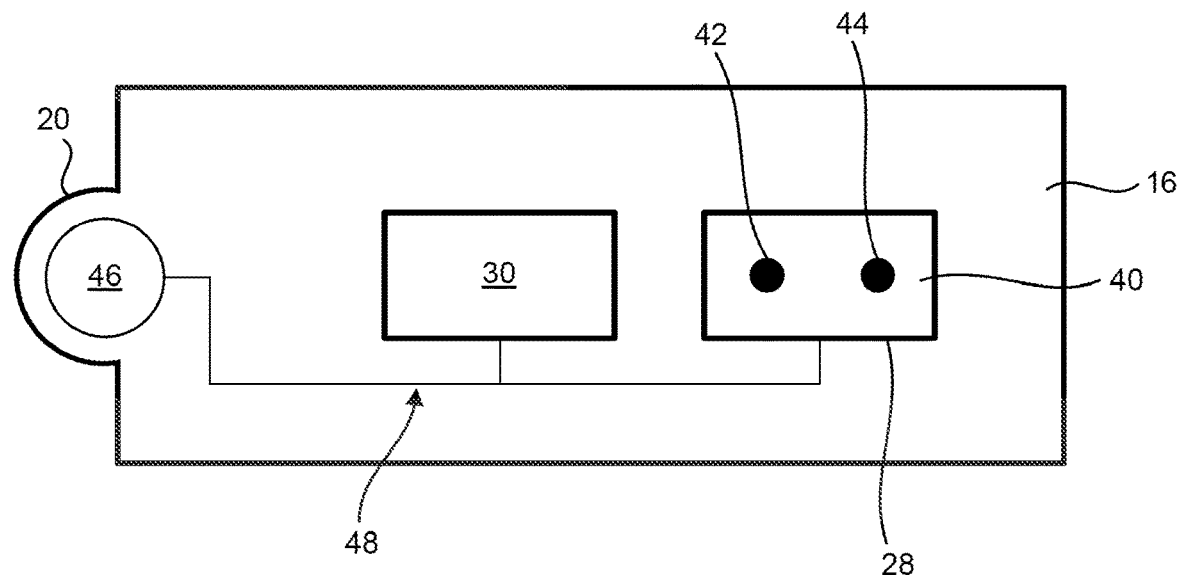
FIG. 4 is a bottom view of a monitoring system for monitoring bodily fluids installed on a user's skin in accordance with the present principles.

Referring to FIG. 4, a detailed bottom view of the sensing layer 16 of the wearable monitoring system 100 is illustrated in accordance with the present principles. The sensing layer 16 may include at least one integrated sensor 28, such as an electrochemical sensor, that touches the skin of the user. The sensor 28 may include a bipolar junction transistor (BJT) with an extended base forming the sensing surface 40. For example, the sensor 28 may include an emitter electrode 42 and a reference electrode 44. In some embodiments, the sensing surface 40 may include a silver chloride (AgCl) material for chloride ion detection. The sensor 28 is placed directly on the user's skin in a location where the positive electrode 32 was previously located such that the sensor 28 comes into contact with bodily fluids secreted by the user. In some embodiments, only the sensing surface 40 and reference electrode 44 come into contact with the user's skin and/or bodily fluids. The sensing surface 40, which may be approximately 1 $cm^2$, and reference electrode surface 44, which may be approximately 2 $mm^2$, may protrude from the surface of the sensing layer 16 and be placed directly on the user's skin.

As illustrated in FIG. 4, the sensing layer 16 may include a battery 46 which may be coupled to the sensor 28 and an RF transmitter via connections 48. The battery 46 may provide a sensing current (e.g., voltage) to the sensor 28 to provide sensing measurements of the bodily fluids. In an embodiment, the reference electrode 44 has a collector voltage of 0 Volts (V) and the emitter electrode 42 is set at a fixed voltage, such as approximately 0.5 V for a npn BJT. When the sensing current is applied to the sensor 28, the sensor 28 detects and/or monitors amounts of and/or concentration levels of bodily fluids (e.g., sweat), such as chloride concentration, secreted by the user through the user's skin.

The sensing layer 16 may further include radio frequency (RF) capability to wirelessly transmit bodily fluid information to a remote location for analysis. For example, the sensing layer 16 may include a radio frequency microelectromechanical system (REMEMS) 30 which may provide radio frequency functionality. The RF transmitter 30, which may be coupled to the sensor 28, may transmit bodily fluid information to a remote location for analysis, such as a computer processing device and/or cellular telephone. Accordingly, the bodily fluid information collected by the sensor 28 is transmitted by radio-frequency signals to a processing device where the bodily fluid data may be analyzed and/or reviewed by a doctor and/or technician. The bodily fluids are employed to monitor health, status and/or functionality by analyzing the measured bodily fluid concentration levels directly at the user's skin. For example, the bodily fluid information may be analyzed to determine if the results are positive or negative for Cystic Fibrosis.

Figure 5:
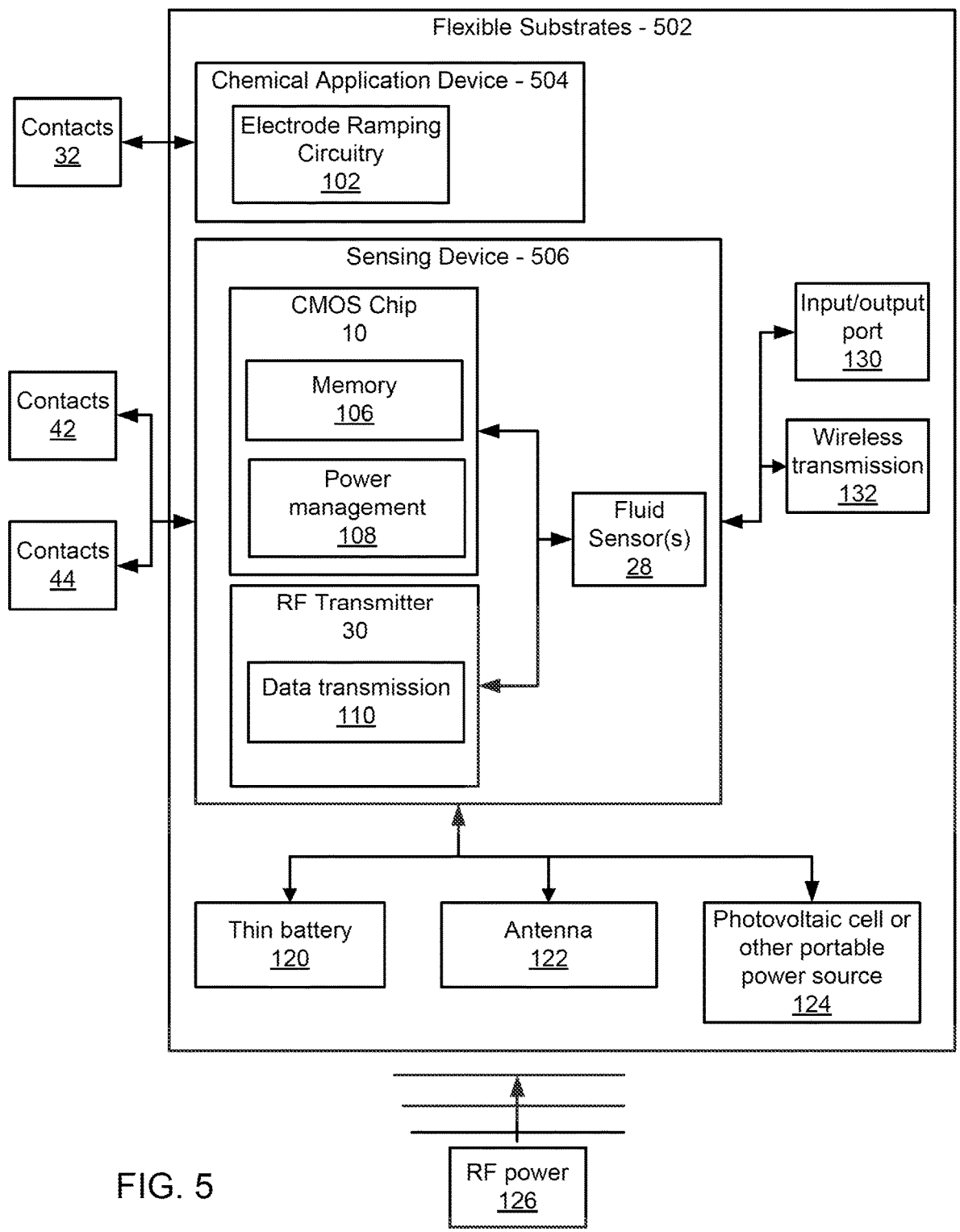
FIG. 5 is a block/flow diagram showing a schematic for a monitoring system for monitoring bodily fluids in accordance with the present principles.

Now referring to FIG. 5, a schematic diagram illustratively depicts the system 500 in accordance with the present principles. System 500 includes flexible substrates 502, which may include a chemical application device 504 and a sensing device 506.

The chemical application device 504 may include electrode ramping circuitry 102 to provide a small current to contacts 32 to drive a chemical substance into a user's skin. For example, electrode ramping circuitry 102 may provide a small current to contacts 32. The current may include an approximate range of 0 to 5 milliamperes (mA), with 0.5 mA to 4 mA being preferable so as not to cause harm to the user. In some embodiments, the current is incrementally ramped slowly from a current of 0.5 mA to a current of 4 mA.

The sensing device 506 may include a radio frequency (RF) transmitter 30 electrically connected to a CMOS chip 10 and one or more fluid sensors 28. The RF transmitter 30 and the CMOS chip 10 may be electrically connected using flip chip package technology. The RF transmitter 30 functions as a radio-frequency (RF) transmitter for data transmission 110. The fluid sensors 28 may detect and/or provide sensing measurements and/or concentration levels of bodily fluids secreted from the user's skin, such as chloride concentration levels.

The CMOS chip 10 includes field effect transistors forming circuits for performing power management. The CMOS chip 10 may include an application specific integrated circuit (ASIC) configured to receive and/or store data from the fluid sensors 28, RF transmitter 30, or other data sources. The CMOS chip 10 includes a memory or storage media 106, which may include random access memory (RAM), solid state memory or other memory types.

The memory 106 may store monitored data or act as a buffer for transmission of data by wireless transmission through a transmission port 132 or input/output port 130. Transmission data protocols, handshaking and data transmission are controlled by a data transmission circuit 110. The data transmission circuit 110 transmits data via input/output port 130 or wirelessly through wireless transmission port 132. The wireless transmission port 130 may include an antenna. For low power embodiments, wireless transmission may be performed locally to a nearby recording device or network.

The CMOS chip 10 may include a power management circuit 108. The power management circuit 108 distributes power to the components of the sensing device 506. In one embodiment, the power for the chemical application device 504 and/or sensing device 506 is obtained using an RF source 126 and an electret receiver/antenna 122, which receives the RF energy and converts the energy to a useable current/voltage to power the system 500. The battery-free tag or antenna 122 is employed to harvest energy from RF transmitters 126 to power the system 500. The RF transmitters 126 may include energy from cell phones or dedicated wireless RF transmitters that may be fixed or portable to power the system 500.

In other embodiments, power can be stored on the thin battery 120 without the use of other power sources. In other embodiments, other power sources may be employed including photovoltaic cells or other portable sources 124. The power source may include a wearable power source or a remote power source. The power source may be disposable or rechargeable.

The antenna 122, battery 120 and/or photovoltaic cells or other portable sources 124 may be employed together or independently. One or more of these power sources may be present and may be formed of or in the flexible substrates 502.

The chemical application device 504 and/or sensing device 506 may include contacts 32, 42, 44 that touch the skin of the user. The contacts 32, 42, 44 may include a corrosion resistant material or metal.

In accordance with the present principles, the system 500 is adhered to a user. Upon activation, the system 500 begins to monitor bodily fluids secreted through the user's skin. The bodily fluids are employed to monitor health, status and/or functionality by analyzing the measured bodily fluid concentration levels directly at the user's skin. The fluid sensors 28 measure the bodily fluid concentration levels and such measurements are transmitted by the RF transmitter 30 using one or more ports 130, 132 and/or wirelessly. The wearable system 500 is configured for continuous monitoring of bodily fluids. The system 500 may be employed for medical monitoring, baseline monitoring, activity monitoring, informational monitoring, etc.

Figure 6:
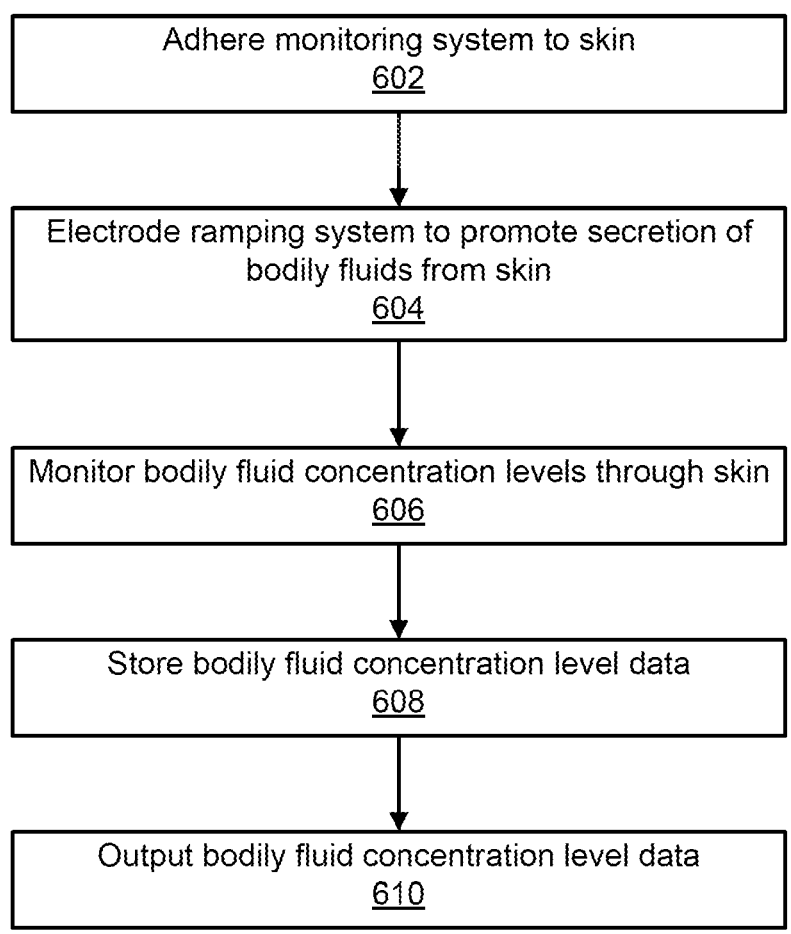
FIG. 6 is a block/flow diagram showing methods for monitoring bodily fluids in accordance with the present principles.

Referring to FIG. 6, methods for monitoring bodily fluids are illustratively shown in accordance with the present principles. In block 602, a monitoring system is adhered to skin of a user using one or more flexible substrates to encapsulate and affix a chemical application device and/or a sensing device to receive bodily fluid data.

In block 604, the monitoring system is powered using a portable power source disposed in or on one or more of the flexible substrates to provide a small current (e.g., 0.5 mA to 4 mA) between electrodes to promote bodily fluids to secrete from the user's skin. The portable power source may include, e.g., a battery-free tag for harvesting energy from radiofrequency signals, a thin battery, a photovoltaic cell, etc. In some embodiments, the small current forces positively charged ions from a chemical substance to move outward from the positive electrode and into the skin of the user. The current may be incrementally increased (e.g., ramped) slowly from a current of 0.5 mA to a current of 4 mA.

In block 606, bodily fluids secreted by the user are detected and/or monitored through the skin of the user. For example, bodily fluids concentration levels may be monitored to determine chloride concentration levels in sweat. The bodily fluids may be collected by a plurality of sensor systems. In block 608, the bodily fluids and/or concentration levels are stored on the integrated circuit chip. The integrated circuit chip may include memory to store data or to buffer data for wireless or wired transmission.

In block 610, the bodily fluids or bodily fluids concentration levels from the monitoring system may be output to a remote device using a wireless transmitter and/or an input/output port. Wireless transmission may occur while the user is wearing the monitoring system in accordance with a wireless protocol (using the data transmission circuit 110). The monitoring system may be plugged into using the input/output port. Data may be read from the monitoring system (while being worn or after being removed) using the input/output port. The data may be transferred to a computer, a network, a cellular telephone, or any other suitable device. Triangulation methods may be employed to determine where the sounds originated from (e.g., when multiple systems are employed).

Having described preferred embodiments system for continuous, periodic and/or intermittent monitoring of bodily fluids (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A wearable monitoring system, comprising:
a collection of layers including a plurality of flexible substrate layers, the plurality of flexible substrate layers including:
a first flexible substrate encapsulating a current ramping system to provide a current to at least one electrode in direct contact with a predetermined location of skin of a user to promote bodily fluid secretion; and
a second flexible substrate placed over the predetermined location and having an integrated electrochemical sensor to determine bodily fluid concentration levels of one or more electrolytes secreted through the skin, the first flexible substrate having a first tab and the second flexible substrate having a second tab, the first tab and the second tab being coupled.

2. The system as recited in claim 1, wherein the first flexible substrate includes at least one chemical substance such that the at least one chemical substance is applied directly on the predetermined location of the skin.

3. The system as recited in claim 2, wherein the current ramping system causes the at least one chemical substance to be absorbed in the predetermined location of the skin.

4. The system as recited in claim 2, wherein the at least one chemical substance includes approximately 2 grams per liter to 5 grams per liter of pilocarpine nitrate.

5. The system as recited in claim 1, further comprising an alignment layer disposed on the first flexible substrate and applied directly on the skin of the user to provide a boundary indicating the predetermined location where the first flexible substrate was applied.

6. The system as recited in claim 1, further comprising a third flexible substrate disposed between the first flexible substrate and the second flexible substrate.

7. The system as recited in claim 6, wherein the third flexible substrate includes a cleaning agent to cleanse the predetermined location.

8. The system as recited in claim 6, wherein the third flexible substrate includes an adhesive agent to remove one or more layers of hair and/or skin from the predetermined location.

9. The system as recited in claim 1, wherein the integrated electrochemical sensor is disposed on a sensing surface, the sensing surface having a silver chloride (AgCl) material for chloride ion detection.

10. The system as recited in claim 1, further comprising a radio frequency micro-electromechanical system to transmit the bodily fluid concentration levels to a remote device.

11. The system as recited in claim 1, further comprising an integrated circuit chip having memory for storing the bodily fluid concentration levels.

12. A wearable monitoring system, comprising:
a collection of layers including a plurality of flexible substrate layers, the plurality of flexible substrate layers including:
a first flexible substrate encapsulating a current ramping system to provide a current to at least one electrode in direct contact with a predetermined location of skin of a user to promote bodily fluid secretion; and
a second flexible substrate placed over the predetermined location, the second flexible substrate having an integrated electrochemical sensor to determine bodily fluid concentration levels secreted through the skin, the first flexible substrate having a first tab and the second flexible substrate having a second tab, the first tab and the second tab being coupled.

13. The system as recited in claim 12, wherein the first flexible substrate includes at least one chemical substance such that the at least one chemical substance is applied directly on the predetermined location of the skin and the at least one chemical substance includes approximately 2 grams per liter to 5 grams per liter of pilocarpine nitrate.

14. The system as recited in claim 12, further comprising an alignment layer disposed on the first flexible substrate and applied directly on the skin of the user to provide a boundary indicating the predetermined location where the first flexible substrate was applied.

15. The system as recited in claim 12, further comprising a third flexible substrate disposed between the first flexible substrate and the second flexible substrate.

16. The system as recited in claim 12, further comprising a radio frequency micro-electromechanical system to transmit the bodily fluid concentration levels to a remote device.

17. A method for monitoring body fluids, comprising:
adhering a monitoring system including a plurality of flexible substrate layers to skin of a user using a first flexible substrate to encapsulate a current ramping system; powering the current ramping system using a portable power source disposed in or on the first flexible substrate to provide a current to at least one electrode in direct contact with a predetermined location of the skin of the user to promote bodily fluid secretion, the first flexible substrate including at least one chemical substance disposed on a first side of the first flexible substrate; and
monitoring bodily fluid concentration levels secreted through the skin using a second flexible substrate of the monitoring system placed over the predetermined location, the second flexible substrate having an integrated electrochemical sensor to determine the bodily fluid concentration levels secreted through the skin, the first flexible substrate having a first tab and the second flexible substrate having a second tab, the first tab and the second tab being coupled.

18. The method of claim 17, wherein the at least one chemical substance is applied directly on the predetermined location of the skin.

19. The method of claim 17, wherein monitoring bodily fluid concentration levels includes detecting one or more chloride ions in the bodily fluid concentration levels.

20. The method as recited in claim 17, further comprising outputting the bodily fluid concentration levels from the monitoring system to a remote device using a wireless transmitter.

* * * * *